United States Patent [19]

Wollweber et al.

[11] Patent Number: 4,935,416
[45] Date of Patent: Jun. 19, 1990

[54] 1-AMINOMETHYL-3-ARYL-4-CYANO-PYRROLES

[75] Inventors: Detlef Wollweber, Wuppertal; Wilhelm Brandes, Leichlingen; Stefan Dutzmann, Duesseldorf; Gerd Hänssler, Leverkusen, all of Fed. Rep. of Germany

[73] Assignee: Bayer Aktiengesellschaft, Leverkusen, Fed. Rep. of Germany

[21] Appl. No.: 300,390

[22] Filed: Jan. 23, 1989

Related U.S. Application Data

[62] Division of Ser. No. 146,876, Jan. 22, 1988, Pat. No. 4,849,435.

[30] Foreign Application Priority Data

Jan. 31, 1987 [DE] Fed. Rep. of Germany ....... 3702853

[51] Int. Cl.⁵ .................. A01N 43/36; C07D 401/06
[52] U.S. Cl. ..................................... 514/212; 540/602
[58] Field of Search ......................... 514/212; 540/602

[56] References Cited

U.S. PATENT DOCUMENTS 4,546,099  10/1985  Nyfeler ................ 514/212

Primary Examiner—Mary C. Lee
Assistant Examiner—J. Haley
Attorney, Agent, or Firm—Sprung Horn Kramer & Woods

[57] ABSTRACT

Fungicidally active novel 1-aminomethyl-3-aryl-4-cyano-pyrroles of the formula

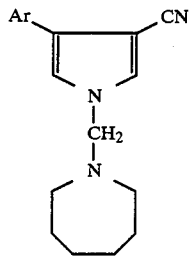

in which
AR represents optionally substituted phenyl.

7 Claims, No Drawings

1-AMINOMETHYL-3-ARYL-4-CYANO-PYRROLES

This is a division of application Ser. No, 146,876, filed Jan. 22, 1988 now U.S. Pat. No. 4,849,435.

The invention relates to new 1-aminomethyl-3-aryl-4-cyano-pyrroles, several processes for their preparation and their use as pesticides.

It has already been disclosed that certain dithiocarbamates such as, for example, zinc ethylene-1,2-bis-(dithiocarbamate) or manganese ethylene-1,2-bis-(diothiocarbamate) or manganese ethylene-1,2-bis-(diothiocarbamate), have good fungicidal properties (cf. for example, K. H. Büchel, "Pflanzenshutz und Schädlingsbekämpfung" [Plant protection and combating of pests], p. 137, 138, Thieme Verlag, Stuttgart 1977). It has furthermore been disclosed that certain sulphenamides, such as, for example, N,N-dimethyl-N'-phenyl-N'-(fluorodichloromethylsulphenyl)-sulphamide, are highly active, in particular, against Botrytis (cf. for example, K. H. Büchel "Pflanzenschutz und Schädlingsbekäampfung", [Plant protection and combating of pests], p. 141, Thieme Verlag Stuttgart 1977).

However, the activity of these previously known compounds is not completely satisfactory in all areas of application, in particular at low application rates and concentrations.

It has furthermore been disclosed that certain 3-aryl-pyrroles, such as, for example, 4-cyano-3-(2,3-dichlorophenyl)-pyrrole, likewise have good fungicidal properties (cf. for example, EP 174,910 or EP 182,738 or EP 133,247).

New 1-aminomethyl-3-aryl-4-cyano-pyrroles of the general formula (I)

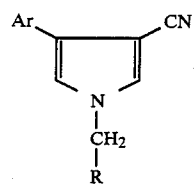

in which
Ar represents optionally substituted phenyl, and
R represents a

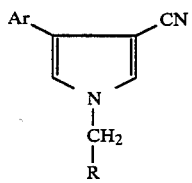

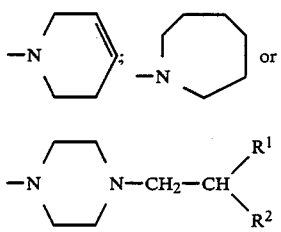

radical,
where
$R^1$ represents hydrogen or alkyl and
$R_2$ represents cyano, alkanoyl, alkoxycarbonyl, alkylaminocarbonyl, dialkylaminocarbonyl, alkylsulphinyl, alkylsulphonyl, phenylsulphinyl or phenylsulphonyl,
have been found.

It has furthermore been found that the new 1-aminomethyl-3-aryl-4-cyano-pyrroles of the general formula (I)

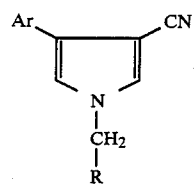

in which
Ar represents optionally substituted phenyl, and
R represents a

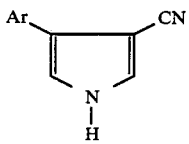

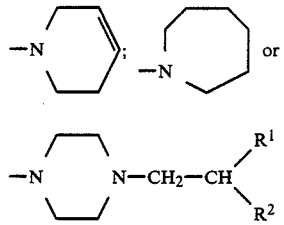

radical,
where
$R^1$ represents hydrogen or alkyl and
$R^2$ represents cyano, alkanoyl, alkoxycarbonyl, alkylaminocarbonyl, dialkylaminocarbonyl, alkylsulphinyl, alkylsulphonyl, phenylsulphinyl or phenylsulphonyl,
are obtained when
(a) 3-aryl-4-cyano-pyrroles of the formula (II),

in which
Ar has the abovementioned meaning,
are reacted with formaldehyde and amines of the formula (III)

R—H    (III)

in which
R has the abovementioned meaning,
if appropriate in the presence of a diluent and if appropriate in the presence of a reaction auxiliary, or when
(b) 3-aryl-4-cyano-pyrroles of the formula (IV)

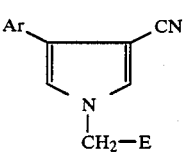

in which
Ar has the abovementioned meaning, and
E represents an electron-withdrawing leaving group, are reacted with amines of the formula (III)

H—R (III)

in which

R has the abovementioned meaning,
if appropriate in the presence of a diluent and if appropriate in the presence of an acid-binding agent.

Finally, it has been found that the new 1-amino-methyl-3-aryl-4-cyano-pyrroles of the general formula (I) have a good action against pests.

Surprisingly, the 1-aminomethyl-3-aryl-4-cyano-pyrroles of the general formula (I) according to the invention, besides a better fungicidal activity compared to previously known dithiocarbamates or sulphenamides from the prior art, such as, for example, zinc ethylene-1,2-bis(dithiocarbamate) or manganese ethylene-1,2-bis(dithiocarbamate) or N,N-dimethyl-N'-phenyl-N'-(fluorodichloromethylsulphenyl)sulphamide, at the same time have a markedly improved crop plant compatibility compared to the previously known 3-aryl-pyrroles from the prior art, such as, for example, 4-cyano-3-(2,3-dichlorophenyl)pyrrole, which are similar compounds chemically and/or regarding their action.

Formula (I) provides a general definition of the 1-aminomethyl-3-aryl-4-cyano-pyrroles according to the invention. Preferred compounds of the formula (I) are those in which Ar represents phenyl which is optionally mono-substituted to poly-substituted by identical or different substituents, suitable substituents being: halogen, in each case straight-chain or branched alkyl, alkoxy, alkylthio, halogenoalkyl, halogenoalkoxy or halogenoalkylthio in each case having 1 to 4 carbon atoms and, if appropriate, 1 to 9 identical or different halogen atoms, and R represents a

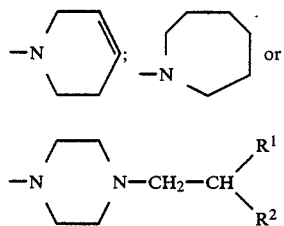

radical, where

R$^1$ represents hydrogen or straight-chain or branched alkyl having 1 to 6 carbon atoms and R$^2$ represents cyano or in each case straight-chain or branched alkanoyl, alkoxycarbonyl, alkylaminocarbonyl, dialkylaminocarbonyl, alkylsulphinyl or alkylsulphonyl in each case having 1 to 6 carbon atoms in the individual alkyl parts, or phenylsulphinyl or phenylsulphonyl.

Particularly preferred compounds of the formula (I) are those in which

Ar represents phenyl which is optionally mono-substituted, disubstituted or trisubstituted by identical or different substituents, suitable substituents being: fluorine, chlorine, bromine, methyl, ethyl, n- or i-propyl, n-, i-, s- or t-butyl, methoxy, ethoxy or methylthio, trifluoromethyl, trifluoromethoxy or trifluoromethylthio, and R represents a

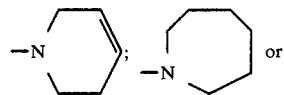

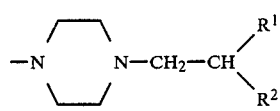

radical, where

R$^1$ represents hydrogen, methyl, ethyl, n- or i-propyl or n-, i-, s- or t-butyl and R$^2$ represents cyano, acetyl, propionyl, methoxycarbonyl, ethoxycarbonyl, methylaminocarbonyl, dimethylaminocarbonyl, ethylaminocarbonyl, diethylaminocarbonyl, dipropylaminocarbonyl, dibutylaminocarbonyl, methylsulphinyl, ethylsulphinyl, methylsulphonyl, ethylsulphonyl, phenylsulphinyl or phenylsulphonyl.

Very particularly preferred compounds of the formula (I) are those in which

Ar represents a 2,3-dichlorophenyl radical, and
R represents a

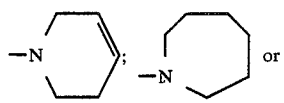

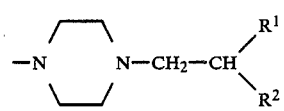

radical, where

R$^1$ represents hydrogen and

R$^2$ represents cyano, acetyl, propionyl, methoxycarbonyl, ethoxycarbonyl, dimethylaminocarbonyl, methylsulphinyl, methylsulphonyl, phenylsulphinyl or phenylsulphonyl.

In addition to the compounds mentioned in the preparation examples, the following 1-aminomethyl-3-aryl-4-cyano-pyrroles of the general formula (I) may be mentioned individually:

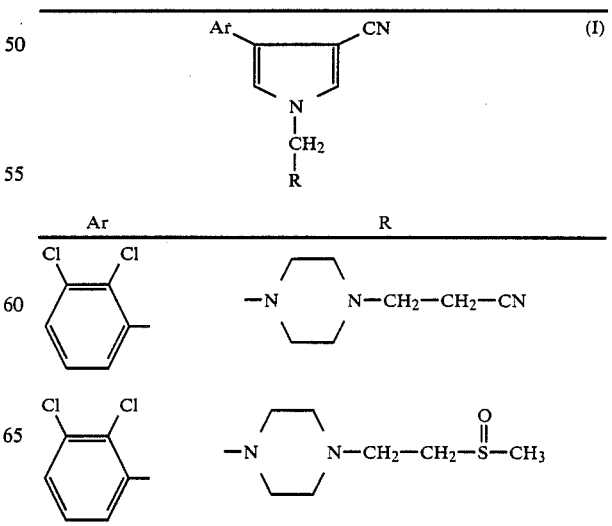

-continued

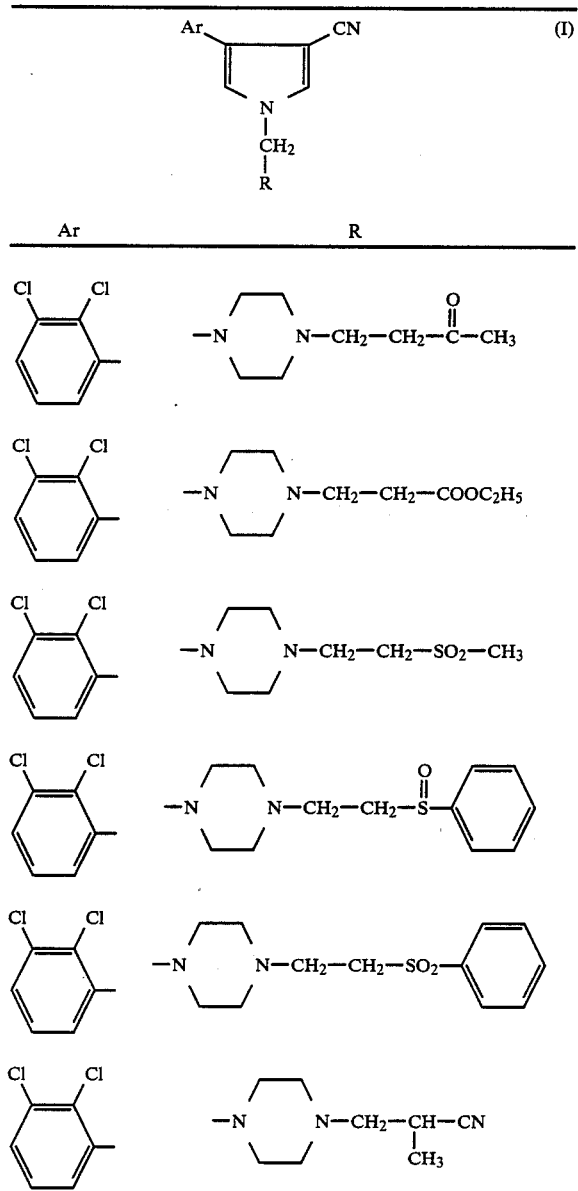

If, for example 4-cyano-3-(2,3-dichlorophenyl)pyrrole, formaldehyde and perhydroazepine are used as starting materials, the course of the reaction of process (a) according to the invention may be represented by the following equation:

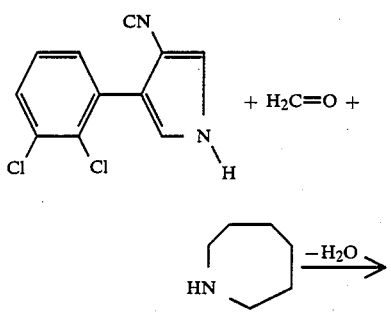

-continued

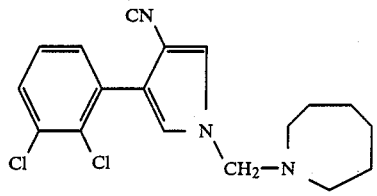

If, for example, 1-chloromethyl-4-cyano-3-(2,3-dichlorophenyl)-pyrrole and tetrahydropyridine are used as starting compounds, the course of the reaction of process (b) according to the invention may be represented by the following equation:

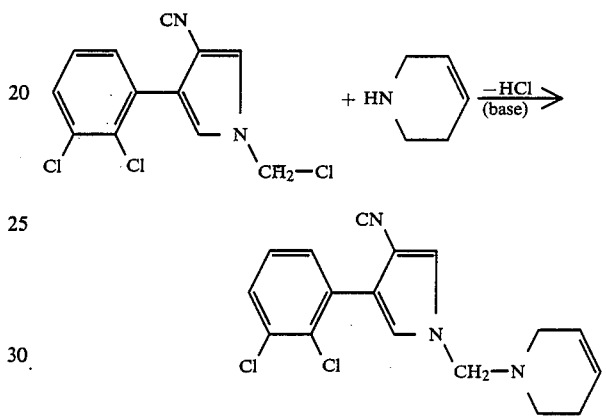

Formula (II) provides a general definition of the 3-aryl-4-cyano-pyrroles which are required as starting materials for carrying out process (a) according to the invention. In this formula (II), Ar preferably represents those radicals which have already been mentioned in connection with the description of the substances of the formula (I) according to the invention as being preferred for these substituents.

The 3-aryl-4-cyano-pyrroles of the formula (II) have been disclosed (cf., for example, EP 174,910, EP 182,738 or EP 133,247).

Formula (IV) provides a general definition of the 3-aryl-4-cyano-pyrroles which are required as starting materials for carrying out process (b) according to the invention. In this formula (IV), Ar preferably represents those radicals which have already been mentioned in connection with the description of the substances of the formula (I) according to the invention as being preferred for these substitutes.

E preferably represents hydroxyl or halogen, in particular chlorine.

The 3-aryl-4-cyano-pyrroles of the formula (IV) have likewise been disclosed (cf., for example, EP 133,247).

Formula (III) provides a general definition of the amines which are furthermore required as starting materials for carrying out processes (a) and (b) according to the invention. In this formula (III), R preferably represents those radicals which have already been mentioned in connection with the description of the substances of the formula (I) according to the invention as being preferred for this substituent.

The amines of the formula (III) are generally known compounds of organic chemistry or can be obtained analogously to generally known processes.

Suitable diluents for carrying out process (a) according to the invention are inert organic solvents or aqueous systems. Protic solvents, for example alcohols, such as methanol, ethanol or propanol, or carboxylic acids, such as formic acid, acetic acid or propionic acid, or mixtures thereof with water, are preferably used. It is also possible to carry out process (a) according to the invention in aprotic solvents. These include, in particular, aliphatic or aromatic, optionally halogenated hydrocarbons, such as, for example, benzine, benzene, toluene, xylene, chlorobenzene, petroleum ether; hexane, cyclohexane, dichloromethane, chloroform or carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

Process (a) according to the invention is carried out, if appropriate, in the presence of a suitable reaction auxiliary. These include either catalytic to equimolar amounts of an organic or inorganic acid or corresponding amounts of a suitable base.

Suitable acidic reaction auxiliaries are, in particularly, inorganic mineral acids, such as phosphoric acid, sulphuric acid, nitric acid, hydrochloric acid or hydrobromic acid, or organic acids, such as formic acid, acetic acid, propionic acid, methanesulphonic acid, benzenesulphonic acid or toluenesulphonic acid.

Suitable basic reaction auxiliaries are all conventional inorganic or organic bases. These include, for example, alkali metal hydroxides, such as sodium hydroxide or potassium hydroxide, alkali metal carbonates, such as sodium carbonate, potassium carbonate or sodium hydrogen carbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

However, it is also possible to simultaneously use the amine of the formula (III) used as a reactant in an appropriate excess as a reaction auxiliary.

The reaction temperatures may be varied within a relatively wide range when carrying out process (a) according to the invention. In general, the process is carried out at temperatures between 0° C. and 120° C., preferably at temperatures between 20° C. and 90° C.

In order to carry out process (a) according to the invention, 1.0 to 2.0 moles, preferably 1.0 to 1.5 moles, of amine of the formula (III) and 1.0 to 2.0 moles, preferably 1.0 to 1.5 moles of formaldehyde are generally employed per mole of 3-aryl-4-cyano-pyrrole of the formula (II). Formaldehyde is employed either in the form of an aqueous solution, as paraformaldehyde or as 1,3,5-trioxane. An aqueous solution is preferably used. The reaction is carried out and the reaction products of the formula (I) are worked up and isolated analogously to known processes (cf. EP 133,247).

Suitable diluents for carrying out process (b) according to the invention are inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofurane or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

Process (b) according to the invention is carried out, if appropriate, in the presence of a suitable acid-binding agent. Suitable as such are all conventional inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

However, it is also possible to simultaneously employ the amine of the formula (III) which is suitable as a reactant in an appropriate excess as a reaction auxiliary.

The reaction temperatures may be varied within a relatively wide range when carrying out process (b) according to the invention. In general, the process is carried at temperatures between 0° C. and 100° C., preferably at temperatures between 20° C. and 60° C.

In order to carry out process (b) according to the invention, 1.0 to 2.0 moles, preferably 1.0 to 1.5 moles, of amine of the formula (III) and, if appropriate, 1.0 to 2.0 moles, preferably 1.0 to 1.5 moles, of acid-binding agent are generally employed per mole of 3-aryl-4-cyano-pyrrole of the formula (IV). The reaction is carried out and the reaction products of the formula (I) are worked up and isolated analogously to known process.

The active compounds according to the invention have a strong action against pests and can be employed in practice for combating undesired harmful organisms. The active compounds are suitable for use, for example, as plant-protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, Septoria nodorum; Leptosphaeria species, such as, for example, *Leptosphaeria nodorum*; Cercospora species, such as, for example, *Cercospora canescens*; Alternaria species, such as, for example, *Alternaria brassicae*; Pseudocercosporella species, such as, for example, *Pseudocercosporella herpotrichoides* and Sclerotinia species, such as, for example, *Sclerotinia sclerotiorum*. The good toleration, by plants, of the active compounds, at the concentrations required for combating plant diseases, permits treatment of above-ground parts of plants, of vegetative propagation stock and seeds, and of the soil.

The active compound according to the invention can be used particularly successfully here for combating cereal diseases, such as, for example, against the pathogen of wheat culm rot (*Fusarium culmorum*), for combating rice diseases, such as, for example, against the pathogen of rice spot disease (*Pyricularia oryzae*) or for combating diseases in fruit and vegetable growing, such as, for example, against the pathogen of grey mold (*Botrytis cinerea*). It should be particularly emphasized here that the active compounds according to the invention, besides a good protective activity, also have systemic properties and are thus also suitable as seed dressings. A good and broad in vitro activity of the compounds and a good tolerance by plants should furthermore be emphasized.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylarly polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

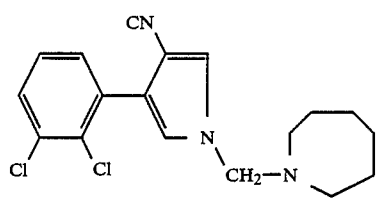

(Process a)

1.6 g (0.02 mole) of a 37 percent strength aqueous formaldehyde solution and 1.9 g (0.02 mole) of hexamethylenimine are added with stirring to 4.0 g (0.017 mole) of 4-cyano-3-(2,3-dichlorophenyl)-pyrrole (cf. EP 133,247) in 17 ml of ethanol. The mixture is refluxed until a clear solution is produced and then stirred for a further 15 hours at room temperature. Work-up is effected by adding 100 ml of water, extracting three times with 50 ml of ethyl acetate in each case, drying the combined organic phases over sodium sulphate and removing the solvent in vacuo. The oil remaining is purified by stirring with hot petroleum ether.

5.5 g (93% of theory) of 4-cyano-3-(2,3-dichlorophenyl)-1-(perhydroazepin-1-yl-methyl)-pyrrole are obtained as an oil. $^1$H-NMR (CDCl$_3$/TMS): δ=4.8 ppm.

The following 1-aminomethyl-3-aryl-4-cyano-pyrroles of the general formula (I) are obtained in a corresponding fashion and according to the general information on the preparation:

USE EXAMPLES

In the following use examples, the compounds shown below were employed as comparison substances:

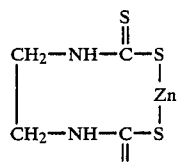

zinc ethylene-1,2-bis-(dithiocarbamate)    (A)

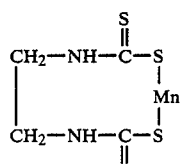

manganese ethylene-1,2-bis-(dithiocarbamate)    (B)

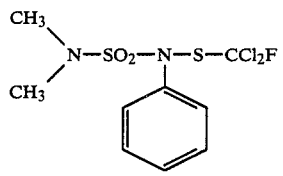

N,N-dimethyl-N'-(fluorodichloromethylsulphenyl)-sulphamide    (C)

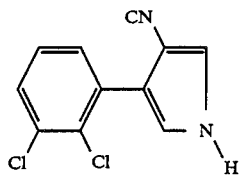

(D)

(1)

| Ex. No. | Ar | R | Physical properties |
|---|---|---|---|
| 2 | 2,3-Cl$_2$-C$_6$H$_3$ | (tetrahydropyridinyl) | $^1$H-NMR*: 4.8 |
| 3 | 2,3-Cl$_2$-C$_6$H$_3$ | piperazinyl-CH$_2$-CH$_2$-CN | oil |

*The $^1$H-NMR spectra were recorded in CDCl$_3$ using tetramethylsilane (TMS) as the internal standard. The chemical shift of the

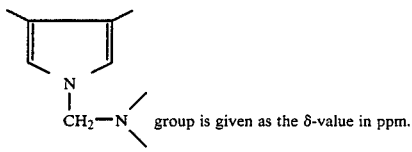

group is given as the δ-value in ppm.

-continued 4-cyano-3-(2,3-dichlorophenyl)-pyrrole (disclosed in EP 174,910).

EXAMPLE A

*Fusarium culmorum* test (wheat)/seed treatment

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

2 batches of 100 grains of the wheat are sown 1 cm deep in standard soil and are cultivated in a greenhouse at a temperature of about 18° C. in seedboxes which are exposed to light for 15 hours daily.

About 3 weeks after sowing, the plants are evaluated for symptoms.

In this test, for example, the compounds according to the following preparation examples exhibit a clearly superior activity compared to the prior art: 1 and 2.

EXAMPLE B

Botrytis test (bean)/protective

Solvent: 4.7 parts by weight of acetone
Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humid chamber at 20° C. 3 days after the inoculation, the size of the infected spots on the leaves is evaluated.

In this test, for example, the compounds according to the following preparation examples exhibit a clearly superior activity compared to the prior art: 1 and 2.

EXAMPLE C

Pyricularia test (rice)/protective

Solvent: 12.5 parts by weight of acetone
Emulsifier: 0.3 parts by weight of alkylaryl polyglycol ether.

To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, for example, the compounds according to the following preparation examples exhibit a clearly superior activity compared to the prior art: 1 and 2.

EXAMPLE D

Plant tolerance test

Test plant: vines
Duration of the test: 6 days
Solvent: 4.7 parts by weight of acetone
Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

Young plants are sprayed with this preparation of active compound until dripping wet and are placed in a greenhouse at about 20° C.

The plants are evaluated for damage, such as impairment of growth, discoloration and necroses. After the specified periods of time, the degree of damage to the plants is determined.

In this test, for example, the compound according to the following preparation example exhibits a clearly superior plant tolerance compared to the prior art: 1.

It will be understood that the specification and examples are illustrative but not limitative of the present invention and that other embodiments within the spirit and scope of the invention will suggest themselves to those skilled in the art.

What is claimed is:

1. A 1-aminomethyl-3-aryl-4-cyano-pyrrole of the formula

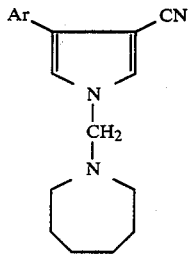

Ar represents phenyl unsubstituted or substituted by at least one of halogen, alkyl, alkoxy, alkylthio, halogenoalkyl, halogenoalkoxy or halogenoalkylthio in each case having 1 to 4 carbon atoms and, if appropriate, 1 to 9 identical or different halogen atoms, $R^1$ represents hydrogen or alkyl having 1 to 6 carbon atoms, and $R^2$ represents cyano, or alkanoyl, alkoxycarbonyl, alkylaminocarbonyl, dialkylaminocarbonyl, alkylsulphinyl or alkylsulphonyl in each case having 1 to 6 carbon atoms in the individual alkyl parts, or phenylsulphinyl or phenylsulphonyl.

2. A 1-aminomethyl-3-aryl-4-cyano-pyrrole according to claim 1, in which
Ar represents phenyl unsubstituted or monosubstituted, disubstituted or trisubstituted by at least one of fluorine, chlorine, bromine, methyl, ethyl, n- or i-propyl, n-, i-, s- or t-butyl, methoxy, ethoxy or methylthio, trifluoromethyl, trifluoromethoxy, or trifluoromethylthio.

3. A 1-aminomethyl-3-aryl-4-cyano-pyrrole according to claim 1, in which

Ar represents a 2,3-dichlorophenyl radical.

4. A compound according to claim 1, wherein such compound is 4-cyano-3-(2,3-dichlorophenyl)-1-(perhydroazepin-1-yl-methyl)-pyrrole of the formula

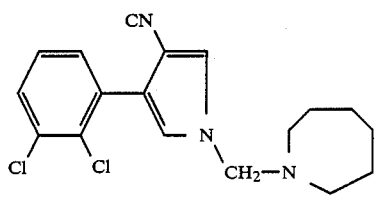

5. A fungicidal composition comprising a fungicidally effective amount of a compound according to claim 1 and a diluent.

6. A method of combating fungi which comprises applying to such fungi or to a fungus habitat a fungicidally effective amount of compound according to claim 1.

7. The method according to claim 6, wherein such compound is 4-cyano-3-(2,3-dichlorophenyl)-1-(perhydroazepin-1-yl-methyl)-pyrrole.

* * * * *

UNITED STATES PATENT AND TRADEMARK OFFICE
CERTIFICATE OF CORRECTION

PATENT NO. : 4,935,416

DATED : June 19, 1990

INVENTOR(S) : Wollweber et al.

It is certified that error appears in the above-identified patent and that said Letters Patent is hereby corrected as shown below:

Col. 14, claim 1  Line 53 after " atoms " delete " , " and substitute
lines 53-60       -- . -- and cancel the balance of the claim.

Signed and Sealed this

Eighteenth Day of February, 1992

*Attest:*

HARRY F. MANBECK, JR.

*Attesting Officer*  Commissioner of Patents and Trademarks